United States Patent [19]

Moy

[11] 4,242,520
[45] Dec. 30, 1980

[54] PROMOTED METHOD FOR PRODUCING CARBAMATES

[75] Inventor: David Moy, Ridgewood, N.J.

[73] Assignee: Halcon Research & Development Corporation, New York, N.Y.

[21] Appl. No.: 7,105

[22] Filed: Jan. 29, 1979

[51] Int. Cl.³ .............. C07C 125/063; C07C 125/07
[52] U.S. Cl. .................................. 560/24; 560/9; 560/25; 560/26; 560/27; 560/28; 560/32; 560/33; 560/115; 560/132; 560/135; 560/136; 560/137; 560/148; 560/157; 560/158; 560/159; 560/161; 560/162; 560/165; 260/465 D
[58] Field of Search .................. 560/24, 25, 32, 33, 560/115, 157, 158, 27, 28, 26, 9; 260/465 D

[56] References Cited

U.S. PATENT DOCUMENTS

| | | | |
|---|---|---|---|
| 3,338,956 | 8/1967 | Mountfield | 560/24 |
| 3,384,655 | 5/1968 | Anderson et al. | 560/24 |
| 3,448,140 | 6/1969 | Gomlen et al. | 560/24 |
| 3,895,054 | 7/1975 | Zajacek et al. | 560/25 |
| 3,956,360 | 5/1976 | Zajacek et al. | 560/24 |
| 3,993,685 | 11/1976 | Zajacek et al. | 560/24 |
| 4,052,437 | 10/1977 | Licke | 560/24 |
| 4,080,365 | 3/1978 | Hiroi et al. | 560/24 |
| 4,134,880 | 1/1979 | Meyata et al. | 560/24 |

*Primary Examiner*—Natalie Trousof
*Assistant Examiner*—G. T. Breitenstein
*Attorney, Agent, or Firm*—William C. Long; David Dick; Jack B. Murray, Jr.

[57] ABSTRACT

A process for the production of carbamates is provided which comprises contacting an organic primary or secondary amine with a source of carbon monoxide, an organic compound containing at least one hydroxyl group and a source of sulfur, selenium or tellurium, in the presence of a catalyst for the reaction and in the presence of at least one member selected from the group consisting of disulfides of the formula $$R^1-S-S-R^2$$

wherein $R^1$ and $R^2$ comprise members selected from the group consisting of alkyl, aryl, cycloalkyl, alkaryl, aralkyl, heterocyclic, alkenyl, alkynyl, alkanoyl, aranoyl, halogenated derivatives of the foregoing groups, and derivatives of the foregoing groups in which one or more carbon atoms is replaced by an oxygen atom.

12 Claims, No Drawings

PROMOTED METHOD FOR PRODUCING CARBAMATES

CROSS-REFERENCE TO RELATED APPLICATION

This application is related to my co-pending application Ser. No. 7,104, filed Jan. 29, 1979, entitled "Improved Process for the Manufacture of Carbamates", filed on even date herewith, the disclosure of which is hereby incorporated by reference.

BACKGROUND OF THE INVENTION

1. Field of the Invention

This invention relates to the preparation of carbamates, and more specifically to the preparation of carbamates by the direct carbonylation of primary and secondary amines.

2. Description of the Prior Art

Carbamates, which are also referred to herein as "urethanes", are industrial chemicals of enormous significance, and much research has been performed in search of economical processes for their manufacture. One such process involves the formation of a primary amine such as aniline from the corresponding organic nitro compound (e.g., nitrobenzene) and reaction of the resulting primary amine with phosgene to form a carbamyl chloride salt which is then thermally decomposed to the corresponding isocyanate. Recovery and reaction of the isocyanate with an alcohol yields the carbamate. Due to the high toxicity of phosgene, and to the corrosive nature of systems in which the chloride ion is employed, alternative processes have been sought which would remove these disadvantages.

Accordingly, a large number of processes were developed to carbonylate an organic nitro compound with carbon monoxide in the presence of an organic hydroxy compound and certain catalyst systems to obtain the corresponding urethane. Exemplary references to these processes and their catalyst systems are as follows: (1) U.S. Pat. Nos. 3,338,956 (carbonyls of metals of Groups VI-B, VII-B and VIII); 3,448,140 (complex compound of a transition metal having atomic number of 21 to 29, 39 to 47 and 71 to 79, inclusive, containing ligands of P, As, or Sb); 3,467,694 (noble metal and a Lewis acid); 3,531,512 (palladium and a Lewis acid); 3,644,462 (noble metal halide and primary, secondary or teritary amine); 3,895,054 (Se, S or Te); 3,956,360 (Se, S or Te); 3,993,685 (tertiary amine and a platinum group metal or compound thereof); 4,052,437 (rhodium oxide) and 4,080,365 (Se+base+aromatic amino or urea promoter); (2) British Pat. Nos. 1,089,132 (metal carbonyls of Groups VI-B, VII-B and VIII and multivalent metals or their salts); 1,469,222 (palladium group metal halide and a nitrogen-containing heterocyclic compound); and 1,485,108 (Se); and (3) French Patent of Addition 2,008,365, as cited in 73 Chem. Abs. 66 302p (1970) (palladium; $Al_2O_3$ or $Fe_2O_3$).

While the above processes allow direct formation of carbamates from nitro-compounds, a one-step process for converting amines to carbamates would also be useful.

Direct carbonylation of aromatic amines to carbamates in significant yields has not heretofore been achieved. Indeed, it was long believed that carbonylation of such amines only yields ureas or formamides. Thus, Hagelloch, Ber., vol. 83, 258 (1950) reacted aniline and COS in ethanol to form low yields (1–3%) of 1,3-diphenyl urea, and German Pat. No. 863,800 (1953) converted aniline to high yields of urea and/or N-substituted formamides with CO in the presence of nickle iodide, powder nickel or cobalt (activated with MgO or $SiO_2$) as catalyst.

U.S. Pat. No. 3,099,689 obtained formamides by reaction of aniline with CO in the presence of organometallic compounds of metals of Groups IVB, VB, VIB, VIIB or VIII of the Periodic Table.

U.S. Pat. No. 4,052,454 formed unsymmetrical ureas by the reaction of nitrogeneous organic compounds with aniline, carbon monoxide and sulfur or selenium and certain bases, and British Pat. No. 1,275,702 produced ureas from primary or secondary mono- or diamines by reaction with CO in the presence of Se. N. Sonoda et al., *J. Amer. Chem. Soc.*, vol. 92 (23), p. 6344 (1971) obtained very high yields of urea from ammonia or aliphatic amines, CO and $O_2$ in the presence of Se, and K. Kondo et al., J. Chem. Soc. Chem. Comm., 307 (1972) obtained stoichiometric yields of urea by carbonylation of aromatic amines with CO, $O_2$ and Se, employing a strongly basic tertiary amine, such as triethyl amine, as co-catalyst.

R. A. Franz et al., 26 *J. Org. Chem.* 3309 (1961) found that tertiary aliphatic amines, KOH and CaO or MgO in methanol were urea catalysts in the reaction of aromatic amines with CO and S. U.S. Pat. No. 2,877,268 disclosed obtention of "excellent yields" of urea by use of alkaline catalysts with a dissociation constant of greater than $1 \times 10^{-10}$: tertiary alkyl amines of 1 to 18 carbon atoms, quaternary ammonium hydroxides, alkaline earth metal and alkali metal hydroxides, alkaline and alkali metal salts (such as sodium oleate), MgO (in methanol), Ca (in methanol) and certain substituted aryl and aralkyl amines. Similarly, diuredides were obtained in Canadian Pat. No. 634,690 by reacting aromatic diamines with CO,S and certain aliphatic or aromatic secondary amines in methanol.

Thio-derivatives of amines have also been produced by carbonylations. U.S. Pat. No. 3,636,104 formed N,N'-diaryl thioureas by reacting aniline with $CS_2$ in pyridine or alcohol with the addition of S or $H_2O$. Alkylamine salts of N-alkyl thiocarbamic acid were prepared in U.S. Pat. No. 2,655,534 by reacting COS and a primary or secondary aliphatic amine. U.S. Pat. Nos. 3,392,197 and 3,539,587 prepared substituted thioureas and monothiocarbamates from primary and secondary amines employing CO and sulfur or sulfur compounds. Thiocarbamates have also been prepared by reaction of amines and disulfides in equimolecular ratio with carbon monoxide in the presence of selenium catalysts and triethylamine. See P. Koch, *Tetrahedron Letters* No. 25, pp. 2087–2088 (1975); West German Patent Publication No. 2,617,917, 86 Chem. Abs. 43426 m (1977).

In attempting to carbonylate amines to a carbamate product, F. Baiocchi, et al., 21 *J. Org. Chem.* 1546 (1956) prepared methyl-N-phenyl carbamate in low yield (27–30%, based on aniline charged) by reacting aniline and COS in methanol employing either zinc peroxide, di-tert-butyl peroxide or $O_2$ to induce the reaction. Magnesium peroxide was found to be not operative, and other peroxides ($H_2O_2$ in $H_2O$ and cumen hydroperoxide in methanol, with and without sodium methoxide), yielded very large amounts of 1,3-diphenyl urea. Netherlands Patent 94,613 converted aliphatic primary and secondary amines to urethanes by reaction with CO in the presence of alcohols and certain stoichiometric amounts of cupric compounds, which are reduced to the cuprous state, and required reoxidation, as by $O_2$, to regenerate the cupric reactant.

R. A. Franz et al., 28 *J. Org. Chem.* 585 (1963) also obtained urethanes from aniline, COS and methanol in the presence of triethyl amine, but could not achieve urethane yields greater than about 13.5%. Even using a carefully controlled, multi-step process, urethane yields greater than 25% were not obtained by Franz et al. under any combination of experimental conditions. Stoichiometric reaction of certain metal acetates ($Hg^{+2}$, $Tl^{+3}$ and $Cu^{+2}$) in T. Saegusa, et al., *Tetrahedron Letters* No. 42, pp. 4123–4126 (1967) with piperidine, CO and $CH_3OH$ did not greatly improve urethane yields. Use of the metal acetates of $Ag^{+1}$, $Cd^{+2}$ and $Zn^{+2}$ gave only trace product, even after 98 hours of reaction.

Higher urethane yields have been provided by U.S. Pat. Nos. 3,384,655 (issued in 1968 to Anderson et al.) and 3,629,311 (issued in 1971 to Anderson et al.) and K. Kondo, et al., *Chem. Letters,* pp. 373–374 (Chem. Soc. Japan 1972). In the Anderson et al. process, a secondary (or a mixture of secondary and teritary) amine is first reacted with COS and an alcohol to form an adduct containing the urea, COS and alcohol, followed by a low temperature oxidation of the adduct with $O_2$, optionally in the presence of soluble Fe, Ni, Co, Cu, Hg, Pd, Pt or Au halide, sulfate or nitrate promoters, to form the desired urethane, elemental sulfur and water. Kondo et al. reacted a primary amine, CO, Se and methanol in the presence of triethylamine, followed by oxidation with $O_2$ of the foregoing mixtures, to yield the urethane, and to form a Se precipitate and water. However, the required use of $O_2$ (or peroxides as in the Baiocchi process) is industrially severely disadvantageous due to the ease with which aniline is oxidized to a wide variety of by-products and due to the obvious explosive hazards associated with mixtures of oxygen, carbon monoxide and alcohol. The explosive hazards require careful attention to temperature controls and use of expensive processing equipment. A further disadvantage to the use of oxygen is the by-product water which is formed and which then reacts with the carbamate to form a urea. To avoid the urea problem, water absorbing agents must be added and additional care must be taken to use anhydrous reactants to avoid further urea being formed. Both of these precautions require added processing expense.

SUMMARY OF THE INVENTION

According to the present invention, yields and selectivities to carbamates in the reaction of an organic primary or secondary amine with a source of carbon monoxide, an organic compound containing at least one hydroxyl group and a source of S, Se or Te, in the presence of a catalyst for the reaction, are greatly improved by providing in the reaction zone at least one disulfide of the formula (I):

$$R^1-S-S-R^2 \qquad (I)$$

wherein $R^1$ and $R^2$ are independently selected from the group consisting of aryl, alkyl, cycloalkyl, alkaryl, aralkyl, heterocyclic, alkenyl, alkynyl, alkanoyl and aranoyl, halogenated derivatives of the foregoing groups, and derivatives of the foregoing groups in which at least one carbon atom is replaced by an oxygen atom.

While certain of the prior art has disclosed polysulfides to be useful as sources of sulfur in the formation of carbamates from aromatic nitro compounds (see, e.g., U.S. Pat. Nos. 3,895,054 and 3,956,360, cited above), it has been found that the organic disulfides of this invention alone do not produce more than trace amounts of carbamate using this invention's amine reactants. Rather, it has been found that these disulfides must be employed in combination with the sulfur, Se or Te sources recited herein to achieve significant yields and selectivities of carbamate. Thus, the combination of such disulfides with such S, Se or Te sources is a synergistic one.

The process of the present invention can achieve surprisingly high yields of carbamate, and has been found to produce the carbamate in selectivities of up to about 90% and more. The process can also produce only very small amounts of ureas, formamides and other by-products. Further, the present invention can achieve the above advantages using very low concentrations of the above metal catalysts, thereby avoiding the requirement of prior art processes in which stoichiometric levels of metal reactants were used. Importantly, the present invention removes the requirement of using molecular $O_2$ or a peroxidic reactant to effect the formation of the carbamate product, minimizing the safety hazards and urea-formation problems attending the use of such reactants.

The process of this invention provides improved carbamate yields over the yields obtained using the process disclosed in my co-pending application Ser. No. 7,104, filed Jan. 29, 1974, referred to above.

DETAILED DESCRIPTION OF THE INVENTION

Any organic primary or secondary amine capable of being converted to an organic carbamate may be employed as a reactant. Aliphatic amines, alicyclic amines and aromatic amines are operable. These amines include primary amines of the formula $RNH_2$ wherein R is alkyl, aryl, alkaryl, aralkyl, and cycloalkyl, and secondary amines of the formula $RNH(R')$ wherein R and R' are independently selected from the group consisting of alkyl, aryl, alkaryl, aralkyl and cycloalkyl. Also included as operable organic amines are primary and secondary amines containing fused rings and heterocyclic substituents. The primary and secondary amines may be substituted or unsubstituted, and when substituted preferably contain inert substituents such as alkyl, aryl, alkaryl, aralkyl, cycloalkyl, halogen (Cl, Br, F and I) cyano, tertiary amino, carboxyl, esters, ethers and thioether groups. Preferably, the amine reactant contains no substitution by OH—, >C=O (i.e., ketonic or aldehydic) or sulfonic acid groups since such groups interfere with the desired carbonylation reaction to the selected carbamates. The foregoing suitable hydrocarbon substituents to the R and R' groups can themselves be substituted by one or more amino groups. Exemplary of such amino substituted hydrocarbyl substituents to the R and R' groups are amino-substituted aralkyls (e.g.,

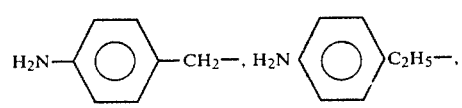

and the like), amino-substituted alkyl (e.g., $H_2NCH(CH_3)$—, $H_2NC_2H_5$— and the like) and amino-substituted alkaryls (e.g.,

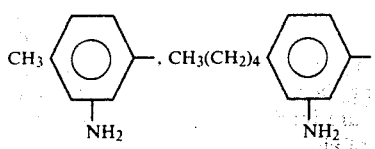

and the like).

Also included as reactants in this invention are amines of the formula $R(NH_2)_m$ wherein R is as defined above and wherein m is an integer of from 1 to 5, preferably of from 1 to 3. Thus, aliphatic, alicyclic and aromatic diamines, such as ethylenediamine, hexamethylenediamine and other homologues and isomers of 2 to 10 carbon atoms are operable. The aromatic diamines include phenylenediamine, toluenediamine and naphthylenediamine. Phenylenetriamine also is operable. Polymeric amines having repeating polymer units based on any of the above amines can also be used (e.g., polymeric methylene dianiline).

Examples of R and R' substituents of the amines of each of the above formulas are alkyl radicals derived from straight and branched-chain alkanes of from 1 to 20, preferably from 1 to 12, carbon atoms (such as methyl, ethyl, isopropyl, butyl, decyl, dodecyl, isostearyl, and the like); aryl of 6 to 18, preferably 6 to 12, carbon atoms (such as phenyl, naphthyl, anthryl and the like), alkaryl and aralkyl of 7 to 24, preferably 7 to 12, carbon atoms (such as benzyl, tolyl, p-butyl phenyl, dihexylphenyl; isostearyl phenyl, and the like) and cycloalkyl of 3 to 12 carbon atoms (such as cyclohexyl, cyclopentyl, cyclobutyl, cyclododecyl and the like).

Typical examples of suitable amines which can be reacted to form carbamates include the following primary amines such as aniline, tolyl amines, xylyl amines, naphthyl amines, anthryl amines, benzyl amine, 1- or 2-bromoethyl benzyl amine, cyclohexylamine, bis-aminoaryl-substituted alkylenes (e.g., compounds of the formula

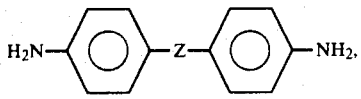

wherein Z is alkylene of 1 to 6 carbon atoms, such as methylene, ethylene, trimethylene, tetramethylene and the like), the diamino toluenes and the like.

Especially preferred as amines in the process of this invention are primary amines of up to 14 carbon atoms. Most preferred are aromatic primary mono- and di-amines of from 6 to 13 carbon atoms. Examples of most preferred monoamines are aniline, and of most preferred diamines are 2,4-diamino-toluene and 4,4'-methylene dianiline.

The source of the carbon monoxide employed as reactant in this invention is not critical and thus carbon monoxide can be employed, in gaseous or liquid form, as a pure material, or in admixtures with other materials which do not adversely affect the desired reaction. For example, carbon monoxide gas can be employed in admixture with materials normally found in synthesis gas (generally containing from about 50 to 80 volume % CO), such as hydrogen, $CO_2$ and the like. Of course, inert gases such as $N_2$, Ar and the like can be employed. The carbon monoxide can also be introduced to the reaction zone in a chemically combined form with one or more of the desired components of the catalyst system. For example, the carbon monoxide can be chemically combined with sulfur as carbonyl sulfide or chemically combined with a metal component of the catalyst system as a metal carbonyl, which under the conditions of the reaction will release carbon monoxide for reaction in the process with the desired amine. Such metal carbonyls are known materials and include Co, Mn and Fe carbonyls. Thus, as used herein, the term "source of carbon monoxide" is intended to refer to CO or a chemically combined or complexed form thereof which releases CO under the conditions of the reaction. Preferred sources of carbon monoxide are CO, COS, COSe, COTe, and metal carbonyls, with COS and mixtures of COS and C0 being especially preferred.

The reaction is preferably conducted in the substantial absence of "reactive oxygen", that is, the amount of molecular oxygen and organic and inorganic peroxides in the reaction zone, whether dissolved, suspended, or in the gaseous state, should be less than 1 weight percent, and preferably less than about 0.1 weight percent, of the amount of amine reactant charged to the reaction zone.

Organic compounds containing at least one hydroxyl group suitable for use in the process in the present invention include mono- or polyhydric alcohols containing primary, secondary or tertiary hydroxyl groups and mixtures thereof. The alcohols can be aliphatic or aromatic and can bear other substituents in addition to hydroxyl groups, but the substituents should, except as hereinafter defined, preferably be non-reactive with carbon monoxide under the process conditions.

Generally, the hydroxyl group-containing compounds comprise compounds of the formula $Z(OH)_n$ wherein n is 1 or more and preferably from 1 to 3, and Z is an optionally substituted aryl, aliphatic, cycloaliphatic or araliphatic group, preferably containing from 1 to 20 carbon atoms, more preferably from 1 to 7 carbon atoms. The group Z can therefore be alkyl, cycloalkyl, alkylene, cycloalkylene, aryl, or aralkyl, which groups can be substituted by alkyl, alkoxy, aryl or aryloxy groups normally containing up to 7 carbon atoms, and derivatives of the foregoing in which one or more carbon atoms are substituted by oxygen, nitrogen, halide ($F^-$, $Cl^-$, $I^-$ or $Br^-$) or sulfur atoms. The foregoing groups can also be substituted by sulfoxide, sulfone, amide, or carboxylic ester groups.

Exemplary hydroxyl group-containing compounds are monohydric alcohols such as methanol, ethanol, n-propanol, sec-propanol, n-iso- and tert-butanol, amyl alcohol, hexyl alcohol, lauryl alcohol, cetyl alcohol, benzyl alcohol, chlorobenzyl alcohol, methoxy benzyl alcohol, methoxy ethanol, butoxy ethanol, cyclohexyl alcohol, phenyl, 2,2,2-trifluoroethanol, alkyl-substituted phenols of 7 to 12 carbon atoms, and the like. Exemplary polyhydric compounds include diols such as ethylene glycol, diethylene glycol, propylene glycol and dipropylene glycol, triols such as glycerol, trimethylolpropane, hexanetriol, tetrols such as pentaerythritol and the like. Ethers of the foregoing polyols can also be employed provided that at least one OH group remains unetherified. The etherifying group in such ether alcohols normally will contain up to 4 carbon atoms and are preferably selected from the group consisting of alkyl, cycloalkyl or aralkyl groups which can themselves be substituted.

Especially suitable hydroxy-containing compounds comprise members selected from the group consisting of the lower monohydric and polyhydric alkanols of 1 to 8 carbon atoms (such as methanol, ethanol, n-propanol, isopropanol, butanol, sec-butanol, isobutanol, ethylene glycol, glycerol, trimethylol propane and the like), halogenated derivatives of the foregoing (such as the trifluoroethanols and the like), phenol and alkyl-substituted phenols having from 1 to 4 carbon atoms in each alkyl-substituent (such as cresol, xylanol and the like).

The process of the present invention also employs in the reaction zone as reactant a "source of sulfur, selenium or tellurium", i.e., a member selected from the group consisting of elemental sulfur, selenium and tellurium, and compounds and complexes thereof. When elemental sulfur, selenium or tellurium are employed, the selected element is preferably used in powdered form. Suitable sulfur compounds which can be employed include organic or inorganic sulfur compounds, exemplary of which are hydrogen sulfide, carbonyl sulfide, sulfur dichloride and the like. Illustrative organic sulfur compounds include the polysulfides having 3 or more S atoms and up to 20 carbon atoms per molecule, e.g., diethyl polysulfide, dioctyl polysulfide and the like. Similarly, suitable selenium compounds include selenium dioxide, selenium trioxide as well as mixtures of the oxides, selenium oxychloride, titanium diselenide, selenium disulfide, sodium selenite, zinc selenite, zinc selenide, tungsten selenide, selenium sulfide, selenic acid and carbonyl selenide. Polyselenides such as diethyl polyselenide and dibutylpolyselenides can also be used. Illustrative tellurium compounds which may be employed include tellurium metal, tellurium oxides, hydrogen telluride, carbonyl telluride and the like.

In the practice of this invention when a source of sulfur is employed in the reaction zone, it has been found that best results are achieved when the reaction zone contains COS and $H_2S$ in a COS to $H_2S$ molar of at least 2:1, and more preferably at least 2.5:1. Likewise, when a Se or Te source is employed in the reaction zone, there is preferably in the reaction zone COSe and H2Se, or COTe and H2Te, in a molar ratio of COS to H2Se (or COTe to H2Te) of at least 2:1, and more preferably at least 2.5:1. Such $H_2S$, H2Se and H2Te compounds will be formed as byproduct in the reaction. If the amount of COS, COTe or COSe which is formed in situ in the reaction zone is not sufficient to attain the above molar ratios in the preferred embodiment, additional amounts of the COS, COSe or COTe can be added directly to the reaction zone to supplement that which is formed in situ.

The foregoing sulfur, selenium and tellurium sources and/or the below-disclosed catalysts, can be self-supported or can be deposited on a support or carrier for dispersing the catalyst to increase its effective surface. Alumina, silica, carbon, barium sulfate, calcium carbonate, asbestos, bentonite, diatomaceous earth, fuller's earth, organic ion exchange resins and analogous materials are useful as carriers for this purpose. Selenium, sulfur or tellurium containing molecular sieves can also be employed as well as complexes of selenium, sulfur or tellurium.

Especially preferred for use in this invention are sulfur sources, most especially COS or elemental sulfur.

The catalysts which are suitable for use in this invention comprise members selected from the group consisting of organic and inorganic bases. Suitable organic bases include members selected from the group consisting of tertiary amines, heterocyclic compounds as defined below, amidines, imines and mixtures thereof.

Exemplary of suitable tertiary amine catalysts are those having the general formula LNL'(L''), wherein L, L' and L'' are independently selected from the group consisting of alkyl of 1 to 20 carbon atoms, aryl of 6 to 18 carbon atoms, alkaryl and aralkyl of 7 to 20 carbon atoms and cycloalkyl of from 3 to 12 carbon atoms. Preferred are the tertiary amines wherein L, L' and L'' are each alkyl of from 1 to 4 carbon atoms. Suitable illustrative tertiary amines are tri-n-propyl amine, triethyl amine, dimethylethyl amine, dimethylpropyl amine, dimethylbenzyl amine, tri-n-butylamine, tri-n-octylamine, triisooctyl-amine, triisononylamine, triisodecylamine, and the like. Suitable heterocyclic compounds include those containing at least one nitrogen atom in the cyclic moiety. Exemplary of such nitrogen-containing basically reacting compounds are pyridine, pyridazine, pyrimidine, pyrazine, piperazine, triazines, tetrazines, pyrrole, isopyrrole, pyrazole, imidazole, quinolines, and the like. Suitable amidines are those having the formula $A^1A^2C=NA^3$ wherein $A^1$, $A^2$ and $A^3$ are independently selected from the group consisting of hydrogen, alkyl of 1 to 20 carbon atoms, aryl of 6 to 18 carbon atoms, aralkyl or alkaryl of 7 to 20 carbon atoms, alkynyl of 2 to 20 carbon atoms and heterocyclic groups (containing N-, S- or O- atoms) of 3 to 5 carbon atoms. Suitable amidines are those having the formula

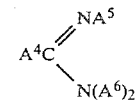

wherein $A^4$, $A^5$ and $A^6$ are independently selected from the group consisting of hydrogen, alkyl 1 to 20 carbon atoms, aryl 6 to 18 carbon atoms, alkaryl or aralkyl 7 to 20 carbon atoms, alkenyl 2 to 20 carbon atoms, alkynyl 2 to 20 carbon atoms, cycloalkyl 3 to 12 carbon atoms, and heterocyclic 3 to 5 carbon atoms. Especially preferred tertiary amine catalysts are pyridine and the dialkylamino pyridines.

Suitable inorganic catalysts comprise at least one member selected from the group consisting of non-halide compounds and complexes of metals of Groups IA, IIA, IVB, VB, VIB, VIIB, VIII, IB, and IIIA of the Periodic Table. Therefore, catalysts which are useful in this invention include compounds and complexes of Li, Be, Na, Mg, K, Ca, Rb, Sr, Cs, Ba, Ti, Zr, Hf, V, Nb, Ta, Cr, Mo, W, Mn, Re, Fe, Ru, Os, Co, Rh, Ir, Ni, Pd, Pt, Cu, Ag, Au, Al, Ga, In and Tl. The compound or complex containing any of the foregoing metals can be inorganic or organic, and mixed salts of the above metals can also be used.

Exemplary of suitable inorganic compounds are the oxides, hydroxides, sulfides, silicates, sulfates, phosphates, arsenides, aresenates, nitrates and the like. Mixed metal salts can also be used, such as the aluminates, titanates, chromates, molybdates, tungstates, gallates and thallates of any of the foregoing metals. Illustrative of inorganic metal salts which can be employed as catalysts are $MoS_2$, $V_2S_3$, $ReS_2$, CuS, $Cu_2S$, $Tl_2SiO_3$, $Cs_3PO_4$, $Cs_2TiO_3$, $Na_2Ga_2O_4$, MnS, $ReSO_4$, PtO, CaS, CsO, Na₂SO₄, Li₂CO₃, Mg₃(PO₄)₂, Tl₂SO₄, ZrO₂, HfO₂, Nb₂O₃, Ta₂O₅, Ru(NO₃)₃, BaO, SrO, IrO, NiS, AgO, Al₂O₃, InO, In₂O₃, and the like. Illustrative of mixed metal salts are CoWO₄, Tl₂O.CoMO₄, CoMo₄, Al₂(CrO₄)₃, NiGa₂O₄, FeTl₂O₄, NiMO₄, BaO.CoMoO₄, BaAl₂O₄, SrWO₄, BaMoO₄, BaCrO₄, Na₂WO₄, K₂O.VWO₄, CsMnO₄, CsFe(SO₄)₂ and the like.

Preferred inorganic catalysts of this invention comprise compounds containing a non-noble metal of Group VIII (i.e., Fe, Co or Ni) together with a metal of Group VIB (i.e., Cr, Mo or W) or Group IIIA (i.e., Al, Ga, In or Tl). Exemplary of such preferred catalysts are CoMoO₄, NiWO₄, FeCrO₃, CoAl₂O₃, NiTl₂O₄ and the like. More preferably, the catalyst also contains an oxide or hydroxide of a metal of Groups IA or IIA, with oxides and hydroxides of Ba, Sr and Cs being most preferred. Exemplary of this class of catalysts are BaO.CoMoO₄, SrO.NiWO₄, CsO.CoMoO₄, SrO.FeCrO₄, NaOH.FeTl₂O₄ and the like. When such oxides and hydroxides of Group IA or IIA metals are employed in admixture with (or chemically combined with) compounds of the foregoing preferred catalysts, the Group IA or IIA metal cation will generally be present in an amount of from about 0.1 to 20 weight percent, preferably from 1 to 10 weight percent, based on the combined weight of the non-Group IA or IIA catalyst metals in the catalyst admixture or chemical combination.

The catalyst can comprise a mixture of at least one inorganic base. Preferably, such mixtures comprises (1) at least one inorganic compound containing a non-noble metal of Group VIII, a Group VIB metal and a metal of Group IA or IIA, together with (2) a heterocyclic amine or a tertiary amine of the formula LNL'(L''), wherein L, L' and L'' are alkyl of 1 to 6 carbon atoms. Exemplary thereof are BaO.CoMoO₄ and pyridine, CsO.CoWO₄ and triethyl amine, SrOH.FeCrO₄ and tri-n-butylamine and the like.

The above catalysts can be pre-treated, if desired, to incorporate the S, Se or Te in the catalyst by contacting the catalyst with a member of the group consisting of hydrogen sulfide, hydrogen selenide and hydrogen telluride, preferably in gaseous form, at elevated temperature to form a catalyst which is chemically combined with the S, Se or Te. This pretreatment step can be performed at a wide variety of temperatures, and generally will be effected at a temperature of from about 150° to 600° C., preferably from about 200° to 400° C. Lower and higher temperatures can also be used. Pressures are not critical and will generally be up to about 1,000 psig or higher. The catalysts can be treated with the selected hydrogen compound for any convenient period, which will generally vary from about 10 to 600 minutes, preferably from about 30 to 180 minutes.

The improved process of this invention achieves its surprisingly improved carbamate yields and selectivities by employing in the reaction zone at least one disulfide of the formula R¹-S-S-R², wherein R¹ and R² are independently selected from the group consisting of alkyl, aryl, cycloalkyl, alkaryl, aralkyl, heterocyclic, alkenyl, alkynyl, alkanoyl, aranoyl, derivatives of the foregoing groups in which one or more carbon-bonded hydrogen is substituted by a halide atom, i.e., F, Cl, I or Br, and derivatives of the foregoing groups in which one or more carbon atom is replaced by an oxygen or nitrogen atom. When "R¹" and "R²" are alkyl, the alkyl group will generally be from 1 to 20 carbon atoms, preferably from 1 to 8 carbon atoms. Exemplary of such alkyl groups are methyl, ethyl, isobutyl, hexyl, octyl, 2-ethyl pentyl, dodecyl and the like. When "R¹" and "R²" are aryl, the aryl group will generally be from 6 to 18 carbon atoms, and preferably from 6 to 12 carbon atoms. Exemplary of such aryl groups are phenyl, naphthyl and anthryl. When "R¹" and "R²" are alkaryl or aralkyl, the groups will generally be from 7 to 12 carbon atoms, preferably from 7 to 9 carbon atoms. Exemplary of such groups are tolyl, benzyl, p-butylphenyl, 2,4-diisopropylphenyl and the like. When "R¹" and "R²" are cycloalkyl, the cycloalkyl group will generally be from 3 to 12 carbon atoms. Exemplary of such groups are cyclohexyl, cyclooctyl, methyl-cyclohexyl, cyclododecyl and the like. When "R¹" and "R²" are alkenyl or alkynyl, the groups will generally contain from 2 to 20 carbon atoms, and preferably from 2 to 8 carbon atoms. Exemplary alkenyl groups are CH₂=CH—, (CH₃)₂C=CH—, CH₃CH=CHCH₂—, hexenyl, octenyl, and the like and exemplary alkynyl groups are CH≡C—, propynyl, hexynyl, decynyl and the like. When "R¹" and "R²" are heterocyclic, the heterocyclic groups will generally contain from 3 to 5 carbon atoms in the cyclic moiety and at least one ring O or N atom. Exemplary of such heterocyclic groups are pyridyl, pyrimidyl, pyrrolidyl, imidazolyl, pyranyl, and the like. When "R¹" and "R²" are alkanoyl (i.e.,

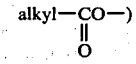

the alkyl moiety will generally contain from 1 to 20 carbon atoms and preferably from 1 to 8 carbon atoms. When "R¹" and "R²" are aranoyl (i.e.,

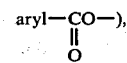

the aryl moiety will generally contain from 6 to 18 carbon atoms, and preferably from 6 to 12 carbon atoms. Exemplary halogenated derivatives of the foregoing groups are fluoro-substituted alkyls, chloro-substituted phenyls and the like. Exemplary ether derivatives of the foregoing are alkoxy-substituted alkyls (such as methoxy-substituted ethyl, butyl and hexyl) and aryls (such as ethoxy-substituted phenyl, cresyl and tolyl) and the like.

Preferred disulfide compounds are the bis-aryl disulfides of 6 to 12 carbon atoms in each aryl moiety and bis-alkyl disulfides of 1 to 4 carbon atoms in each alkyl moiety. Exemplary compounds are phenyl disulfide (φ₂S₂), methyl disulfide ([CH₃]₂S₂), isobutyldisulfide ([(CH₃)₂CH]₂S₂), tolyldisulfide ([CH₃φ]₂S₂), 2,4-dimethylphenyldisulfide

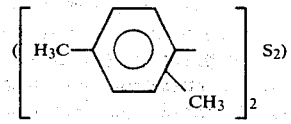

benzyl disulfide

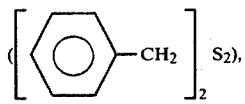

and the like.

The quantity of such disulfide compounds employed in the practice of this invention is not critical and can vary widely. Typically, these disulfides will be employed in an amount sufficient to provide a molar ratio of the disulfide to the amine reactant of at least about 0.1:1, preferably at least about 0.5:1, more preferably at least about 1:1. The maximum amount of disulfide will generally be limited solely by economics. Thus, disulfide will generally be employed in an amount of up to 10 moles of the disulfide per mole of amine reactant, and more preferably in an amount of up to 5 moles of the disulfide per mole of amine reactant.

During the reaction, the disulfides react to form the corresponding thiol which can be readily recovered from the reaction mixture, as by distillation, and oxidized by conventional methods to regenerate the disulfide for recycle to the process if desired.

Water is detrimental to carbamate yields employing the process of this invention, and, therefore, it is preferred to employ substantially anhydrous reaction conditions and to employ as reactants those that are substantially anhydrous, although minor amounts of water introduced, for example, as water of hydration in any of the S, Se or Te sources or metal salts, can be introduced without marked effect on product yield or quality. In general, the amount of water in the reaction zone should be limited to a concentration of less than about 1 weight percent, based on the amine reactant charged to the reaction zone. To effect such desired low levels of water, a water absorbing agent can also be employed in the reaction zone. Suitable water absorbing agents are described in U.S. Pat. Nos. 3,384,655 and 3,629,311. However, use of such water absorbing agents will not generally be necessary since water is not a by-product of the reaction to the desired carbamate. As used herein, the term "in the substantial absence of water" is intended to refer to water concentrations of less than about 1 weight percent, based on the amine reactant charged to the reaction zone.

A wide variety of organic solvents can also be employed in the reaction zone. Suitable organic solvents include alkanes such as cyclohexane, hexane, octane and the like; aromatic solvents such as benzene, toluene, xylene; nitrile solvents such as acetonitrile and benzonitrile; amide type solvents such as N,N-dimethyl formamide and N,N-dimethyl acetamide; aliphatic, alicyclic or aromatic sulfoxide and sulfone solvents, such as dimethyl sulfoxide; aliphatic halogenated hydrocargons such as 1,1,2-trichloro-1, 2-2-trifluoroethane, halogenated aromatic hydrocarbons such as monochlorobenzene, dichlorobenzene and trichlorobenzene; esters; and ether solvents such as tetrahydrofuran, 1,4-dioxane, 1,2-dimethoxyethane and the like. The ether compounds, for example, can be aliphatic, aromatic or heterocyclic, and they can also be either mono or polyethers, or combinations of these compounds. When the hydroxy-containing organic compound is a liquid under reaction conditions, it sometimes can function as a solvent and is generally preferred. The solvent can also comprise the organic base catalyst, such as tertiary amines, heterocyclic compounds, amidines, imines and mixtures thereof, when these are liquids under reaction conditions.

At higher temperatures and pressures the process of the invention can advantageously be carried out in an inert diluent. The preferred inert diluents are those in which the non-gaseous reactants are soluble, including some of the solvents mentioned about. Suitable inert diluents include aliphatic or aromatic hydrocarbons such as n-pentane or toluene, ethers, ketones and esters.

The invention is preferably carried out with at least equal molar amounts of the carbon monoxide and the amine reactant being present. The monohydric hydroxyl-containing organic compounds will generally be used in at least an equimolar amount with the amine reactant, with the mole ratio of monohydric hydroxyl-compound to amine reactant preferably being from at least 2:1 to about 20:1, and most preferably from about 6:1 to 12:1. The amount of polyhydric alcohol which will be generally employed as the hydroxyl-containing organic compound can be determined from the foregoing mole ratios of monohydric alcohol to amine reactant and will of course be based on the number of reactive hydroxyl groups in each molecule of the alcohol, e.g., at least 0.5 mole of ethylene glycol will generally be used for each mole of mono amine reactant in the preparation of the corresponding carbamate derivatives of ethylene glycol. The mole ratio of the S, Se or Te source to the amine reactant can vary over a wide range, e.g., from about 1:10 to 100:1. However, a somewhat more preferred range of moles of S, Se or Te source to amine is from about 1:1 to 10:1. It will be understood that with reference to the "moles" of S, Se or Te source it is meant the element selenium or sulfur and not the compound if the S, Se or Te source is a compound. Likewise with respect to the amine reactant, reference is to the active nitrogen containing group, e.g., the amine group. Thus, if the amine reactant is a diamino compound, for example, ethylenediamine, the number of moles would be one half, i.e., the equivalent ratio.

The inorganic catalysts of this invention when present, will be generally used in an amount (calculated as the catalytically active metal) of at least about 1, and preferably at least about 10, weight percent of the amine reactant charged. While the catalyst can be used in larger concentrations, use of greater than about 50 weight percent will generally be uneconomical. Likewise, while less than 1 weight percent can be used, the reaction rate may be uneconomically low. The organic catalysts of this invention, when present, will generally be used in an amount of at least about 5 weight percent, preferably at least about 20 weight percent, more preferably from about 20 to 40 weight percent, of the amine reactant charged.

The amount of solvent is also not critical and, where used, will generally range from about 1 to 50 weight percent, and preferably from about 1 to 40 weight percent, of the reaction mixture.

The order of mixing the reactants is not critical and can be varied within the limitations of the equipment employed. A simple procedure is to charge the amine reactant, the organic compound containing at least one hydroxyl group, and the S, Se or Te source into the reaction vessel, introduce the proper amount of the source of carbon monoxide and then heat the mixture to obtain the desired reaction. A suitable pressure vessel, such as an autoclave, which is preferably provided with heating means and agitation means, such as a stirrer or an external rocking mechanism, is employed for the reaction.

Generally, the amount of gaseous carbon monoxide in the free space of the reactor is sufficient to maintain the desired pressure as well as to provide a reactant for the process. As the reaction progresses an additional source of carbon monoxide can be fed to the reactor either intermittently or continuously. Although greater and lesser amounts of the source of carbon monoxide can be employed if desired, generally the total amount of the source of carbon monoxide added during the reaction is between about 3 and about 50 moles and preferably between about 8 and about 15 moles of CO per non-cyclic group containing the active amine group of the amine reactant nitrogen atom. The highest carbon monoxide requirements are generally utilized in a process in which carbon monoxide gas is added continuously, but suitable recycle of carbon monoxide containing gas streams greatly reduces the overall consumption of carbon monoxide.

The reaction temperature is generally maintained in the range of from about 60° to about 250° C. and preferably within the range of from about 100° to about 200° C. These temperature ranges permit a convenient rate of reaction to be achieved while avoiding undesirable side reactions. It will be understood, however, that any elevated temperatures below that at which the starting materials or the products decompose can be used. The reaction is carried out, as indicated above, at superatmospheric pressures which is normally between about 10 and about 500 atmospheres, although higher or lower reaction pressures can be employed if other reaction conditions are suitably adjusted. Preferably, however, only moderate carbon monoxide pressures in the range of about 10 to about 100 atmospheres are employed and the reaction is conveniently run at a temperature of below about 200° C. within this pressure range.

The process of the present invention can be carried out batchwise, semi-continuously or continuously. The reaction time is dependent upon the nature of the reactants, temperature, pressure and the type of catalyst employed, as well as the type of equipment which is used. Normally the reaction time is less than 180 minutes and generally the effectiveness of the catalysts of this invention permits the reaction to be completed within a time period between about 10 minutes and about 75 minutes.

The process of this invention can be carried out in a vapor phase or a liquid phase, or partially in vapor and liquid phases in the reaction zone.

After the reaction has been completed in the batchwise practice of this invention, the temperature of the reaction mixture can be dropped to ambient temperature and the pressure vessel vented. The reaction product is then treated by conventional procedures, including filtration, distillation, or other suitable separation techniques, to effect separation of urethane from unreacted starting material, solvent, by-product, catalyst, etc. Urea by-products, if any, can be readily recovered and recycled to the reaction zone, if desired, to suppress formation of the urea by-product therein.

As indicated above, the amount of reaction by-products (e.g., formanilide and ureas when N-phenyl carbamates are the desired product) which are formed in the process of this invention is surprisingly low. While the amount of such N-containing by-products will vary, they will preferably be formed in a slectivity of less than 20 weight percent, more preferably less than 10 weight percent, and most preferably less than 5 weight percent, based on the amine reactant-reacted.

The process of this invention, therefore, preferably forms the desired carbamate product in a selectivity of at least 80 weight percent, more preferably at least 90 weight percent, and most preferably at least 95 weight percent, based on the amount of the amine reactant reacted.

The urethane products obtained by the invention contain one or more urethane groups and can be monomeric or polymeric in nature. Thus, the process of the invention can be adapted for the preparation of monourethanes from monoamine compounds and monohydroxy compounds and adapted for the preparation of polyurethanes from polyamine compounds and monofunctional hydroxy compounds. The resulting urethane products, in particular those urethanes containing not more than three urethane groups per molecule, can be converted to corresponding isocyanates by suitable means, including thermal and catalytic means.

The process of this invention can be further illustrated by the following examples wherein parts are by weight unless otherwise indicated. In the examples, analysis of gas and liquid samples is performed by gas chromatography, with toluene being used in the liquid samples as internal standard.

In the Examples, the $CoMoO_4$ on alumina catalyst are ⅛ in. pellets comprising 3.5 weight percent CoO, 10.0 weight percent $MoO_4$ on gamma-alumina (Strem Chemical Co.) having a surface area of 244 sq. m. per gm. The $BaO.CoMoO_4$ on alumina catalyst is prepared by admixing 25 grams of the above $CoMoO_4$ on alumina pellets with 75 cc of an aqueous solution containing dissoved therein 2.5 grams of $BaOH.8H_2O$. The mixture is then placed in a rotovap at 50° C. to remove the water, and the resulting solids are heated for four hours at a temperature of from about 350° to 400° C. in an oven, to form the $BaO.CoMoO_4$ on alumina. All other catalysts in the Examples are used in powder form, 60–80 mesh.

In Examples 1–11 and 13–25, and elsewhere stated, the $COS:H_2S$, $COS:H_2Se$ and $COTe:H_2Te$ molar ratios (as appropriate) in the reaction zone are at least 2:1.

In the Examples, carbamates (and by-product) yields and selectivities are based on the amounts of the amine reactant charged and reacted, respectively. The sulfur to amine rectant molar ratios are calculated without considering the sulfur content of the disulfide promoters used in the Examples.

EXAMPLE 1

To a 200 cc Parr reactor provided with a glass liner (actual reactor volume with liner=134 cc) and a magnetic stirrer is charged, at room temperature, 1.0 gram aniline, 20 cc methanol, 0.5 gram of $BaO.CoMoO_4$ as catalyst and 2.5 grams of phenyl disulfide ($\phi_2S_2$). The reactor is sealed and then purged with gaseous nitrogen by means of a gas inlet tube and, also at room temperature, gaseous COS (2.5 grams) is pressured into the reactor following which CO is pressured into the reactor, to provide a pressure in the reactor of about 500 psig. The molar ratio of S:aniline in this example is about 2.5:1. The pressured reactor is then heated with stirring by means of an oil bath to a temperature of 180° C., which is measured externally to the reactor. This reaction temperature is maintained for six hours after which the oil bath is cooled to about 30° C. by passing cooling water through a copper tube which is immersed in the bath. The gas in the reactor is then vented and the vent gas and the liquid product mixture in the reactor are analyzed. Methyl N-phenyl carbamate ("MPC") is found to be present in a yield of about 59 percent and in a selectivity of about 95%. No detectable formanilide is formed and the diphenyl urea yield is less than 5%.

EXAMPLE 2

The procedure of Example 1 is repeated except that the catalyst comprises 0.5 gram of $BaAl_2O_4$ and except that 0.5 gram powdered elemental sulfur is used instead of the COS, giving a S:aniline molar ratio of 1.5:1. At the end of the six hours of reaction, methyl-N-phenyl carbamate is found to be present in a yield of about 74%, and in a selectivity of about 95%.

EXAMPLE 3 FOR COMPARISON

The procedure of Examples 1 and 2 are each repeated except that the phenyl disulfide is omitted from the reaction zone. After six hours of reaction at 180° C., the reactor of effluent in each run (i.e., both the vent gas and liquid phases) is analyzed, yielding the data set forth in Table I below:

TABLE I

| Run No. | Catalyst | MPC % Yield | MPC % Selectivity |
|---|---|---|---|
| 1 | $BaO \cdot CoMoO_4$ | 50 | 80 |
| 2 | $BaAl_2O_3$ | 24 | 90 |

EXAMPLE 4

Following the procedure of Example 1, 1.02 grams aniline, 10 cc phenol and 1.0 gram powdered elemental sulfur are reacted in separate runs for 6 hours at 150° C., using a CO pressure of 850 psig, in the presence of the desired catalyst and in the presence of 2.5 grams of phenyl disulfide. The sulfur to aniline molar ratio in each run is 2.8:1. Two runs without phenyl disulfide are made as controls. The data thereby obtained are set forth in Table II.

TABLE II

| Run No. | Catalyst | (amt) | φ Carbamate** % Yield | % Selectivity |
|---|---|---|---|---|
| 1 | TEA* | 5 cc. | 17 | 36 |
| 2 | $BaO \cdot CoMoO_4$ | 0.5 g. | 22 | >95 |
| Control A | TEA* | 5 cc. | 5 | — |
| Control B | $BaO \cdot CoMoO_4$ | 0.5 g. | 5 | — |

*"TEA" = triethylamine
**"φ Carbamate" = phenyl N-phenyl carbamate.

EXAMPLE 5

Following the procedure of Example 1, 1.02 grams aniline, 1.0 gram powdered elemental sulfur and 10 cc 2,2,2-trifluoro-ethanol are reacted in separate runs in the presence of 0.8 gram $SrMoO_4$ as catalyst and the desired disulfide. In each run, a CO pressure of 1,000 psig, a temperature of 180° C. and a reaction time of 6 hours is used. The S:aniline molar ratio is 2.8:1. One run without any disulfide is made as a control. The data thereby obtained are set forth in Table III.

TABLE III

| Run No. | Disulfide | (amt) | Carbamate* % Yield | % Selectivity |
|---|---|---|---|---|
| 1 | Phenyl Disulfide | 2.5 g. | 47 | >95 |

TABLE III-continued

| Run No. | Disulfide | (amt) | Carbamate* % Yield | % Selectivity |
|---|---|---|---|---|
| 2 | n-Butyl Disulfide | 1.9 g. | 13 | >95 |
| 3 | Benzyl Disulfide | 2.7 g. | 26 | >95 |
| Control C | None | — | 5 | 20 |

*Carbamate = 2,2,2-trifluoroethyl-N-phenyl carbamate.

EXAMPLE 6

The procedure of Example 5 is repeated in separate runs except that 5 cc triethylamine is used as catalyst instead of $SrMoO_4$ and the CO pressure is 900 psig. One run is made without any disulfide as a control. Data so obtained are set forth in Table IV.

TABLE IV

| Run No. | Disulfide | (amt) | Carbamate % Yield | % Selectivity |
|---|---|---|---|---|
| 1 | Phenyl Disulfide | 2.5 g. | 64 | 68 |
| 2 | Phenyl Disulfide | 2.5 g. | 42 | 65 |
| 3 | Benzyl Disulfide | 2.7 g. | 38 | 72 |
| 4 | n-Butyl Disulfide | 1.9 g. | 22 | 74 |
| Control D | None | — | 9 | 20 |

EXAMPLE 7

The procedure of Example 6, Run 1 is repeated (using triethylamine and phenyl disulfide) except the reaction mixture also contains 15 cc dioxanes as solvent. After 6 hours of reaction at 150° C., using a CO pressure of 1,000 psig, the yield of 2,2,2-trifluoro-ethyl-N-phenyl carbamate is found to be about 44% and the carbamate selectivity is about 78%.

EXAMPLE 8

Following the procedure of Example 1, 1.02 gram aniline, 10 cc 2,2,2-trifluoro ethanol and 1.0 gram powdered sulfur are reacted at 100° C. for 6 hours using a CO pressure of 1,000 psig, in the presence of 0.5 gram $BaO \cdot CoMoO_4$ as catalyst and 2.5 grams phenyl disulfide. There is thereby produced 2,2,2-trifluoro-ethyl-N-phenyl carbamate in a yield of about 56% and in a selectivity of greater than about 95%.

When the foregoing run is repeated using 2.5 gram COS instead of the elemental sulfur, substantially the same results are obtained.

When either of the foregoing 2 runs are repeated, except that the phenyl disulfide is omitted from the mixture charged to the reaction zone, the carbamate yield in each run is found to be 5%.

EXAMPLE 9

The procedure of Example 1 is repeated employing 0.5 gram of $SrMoO_4$ as catalyst, except that 1.0 gram powdered elemental sulfur is used instead of COS and the CO pressure is 1,000 psig. One run is made without phenyl disulfide as a control. Data thereby obtained are set forth in Table V.

TABLE V

| Run No. | Catalyst | (amt) | Carbamate** % Yield | % Selectivity |
|---|---|---|---|---|
| 1 | $SrMoO_4$ | 0.5 g. | 79 | 95 |
| Control E | $SrMoO_4$ | 0.5 g. | 44 | 90 |

**Carbamate = methyl-N-phenylcarbamate

EXAMPLE 10 FOR COMPARISON

The procedure of Example 9 is repeated using 0.5 g. SrMoO$_4$ as catalyst, except that the powdered sulfur is omitted from the mixture charged to the reaction zone. Thus, the only possible "source" of sulfur in the reaction zone is the 2.5 grams of phenyl disulfide. After 6 hours of reaction at 180° C., using a CO pressure of 1,000 psig, the methyl-N-phenyl carbamate is found to have been produced in only trace amounts.

EXAMPLE 11

Following the procedure of Example 1, 2.5 grams phenyl disulfide, 0.8 gram SrMoO$_4$, 5 cc triethylamine, 1.02 grams aniline, 15 cc 2,2,2-trifluoroethanol and 1 gram powdered sulfur (sulfur: aniline molar ratio = 2.8:1) are charged to the reaction zone and are reacted at a temperature of 180° C. for 6 hours, using a CO pressure of 1,000 psig. The 2,2,2-trifluoroethyl-N-phenyl carbamate is found to be produced in a yield of about 35% and in a selectivity of 90%.

EXAMPLE 12

Run 1. Following the procedure of Example 1, 1.02 grams of aniline, 10 cc methanol and 0.8 grams of SrMoO$_4$ as catalyst, together with 2.5 grams of phenyl disulfide, 1,000 psi CO and 200 psi H$_2$S are charged to the reactor. Analysis of the materials in the reactor shows a COS:H$_2$S mole ratio of 0.67:1. The mixture is then allowed to react to a temperature of about 180° C. for a period of 6 hours, thereby forming methyl-N-phenyl carbamate in a 20% yield.

Run 2. The above procedure is repeated except that sufficient additional COS is pressured into the reactor to provide a COS:H$_2$O molar ratio of 2.0:1. After the 6 hours of reaction time, the methyl-N-phenyl carbamate yield was increased to 40%.

Run 3. In a third run, additional COS is pressured into the reactor to raise the COS:H$_2$O molar ratio to 2.5:1. Analysis of the effluent following the 6 hours of reaction time shows methyl-N-phenyl carbamate to be formed in a yield of about 79% and in a selectivity of greater than about 95%.

EXAMPLE 13

The procedure of Example 6, Run 1 is repeated except that 5 cc of pyridine is used instead of the triethyl amine. After reaction of the mixture at a CO pressure of 900 psig a temperature of 180° C. for a period of six hours, the reaction effluent is found to contain methyl N-phenyl carbamate in a yield of about 30% and in a selectivity of about 60%.

EXAMPLE 14

The procedure of Example 1 is repeated employing 0.5 gram of SrMoO$_4$ as catalyst, except that 1.0 gram powdered elemental sulfur is used instead of COS and the CO pressure is 1,000 psig. After the 6 hours of reaction at 180° C., the reaction effluent is found to contain methyl-N-phenyl carbomate in a yield of about 61%, and in a selectivity of about 79%.

EXAMPLE 15

Following the procedure of Example 1, separate runs are made employing a charge to the reactor of 1.02 grams of aniline, 2.5 grams of COS, 2.5 grams of phenyl disulfide, and 0.5 gram of BaMoO$_4$ as catalyst, together with 10 cc of the selected alcohol and the desired amount of pyridine. Thus, a sulfur to aniline molar ratio of 2.5:1 is used in each run. Employing a CO pressure of 750 psig, the reaction is performed at a temperature of 180° C. for 12 hours, after which the effluent of each run is analyzed, thereby yielding the data set forth in Table VI below.

TABLE VI

| Run No. | Pyridine (cc) | Alcohol | Carbamate % Yield |
|---|---|---|---|
| 1 | 10 | DMAE* | 70 |
| 2 | — | DMA* | 75 |
| 3 | — | Methyl** cellosolv | 80 |

*"DMAE" = dimethyl aminoethanol, (CH$_3$)$_2$NCH$_2$CH$_2$OH,
DMAE carbamate = (CH$_3$)$_2$NCH$_2$CH$_2$OCNH$\phi$.
$$\underset{O}{\overset{\|}{}}$$

**"Methyl cellosolv" = CH$_3$OCH$_2$CH$_2$OH.
Carbamate = CH$_3$OCH$_2$CH$_2$OCNH$\phi$.
$$\underset{O}{\overset{\|}{}}$$

EXAMPLE 16

The procedure of Example 12, run 3 is repeated in separate runs employing the catalysts indicated in Table VII. Analysis of the effluent from each run yields the data set forth in Table VII:

TABLE VII

| Run No. | Catalyst | MPC % Yield |
|---|---|---|
| 1 | MnS | 65 |
| 2 | ReS$_2$ | 60 |
| 3 | PtO | 65 |
| 4 | NiWO$_4$ | 65 |
| 5 | FeCrO$_4$ | 60 |
| 6 | Tl$_2$SiO$_3$ | 70 |
| 7 | Tl$_2$SO$_4$ | 75 |
| 8 | Cs$_3$PO$_4$ | 75 |
| 9 | V$_2$S$_3$ | 70 |
| 10 | TiS$_2$ | 70 |
| 11 | Ti$_2$S$_3$ | 70 |
| 12 | CuS | 60 |
| 13 | MoS$_2$ | 65 |
| 14 | WS$_2$ | 65 |
| 15 | CrS | 55 |

In each run, the methyl-N-phenyl carbamate (MPC) selectivity is found to be from 75 to 80%.

EXAMPLE 17

The procedure of Example 9 is repeated except that 2.5 grams of powdered elemental selenium are employed instead of the elemental sulfur, thereby providing a selenium to aniline molar ratio of about 2.9:1. Essentially no difference in results is noted.

EXAMPLE 18

The procedure of Example 9 is repeated except that 4.0 grams of powdered elemental tellurium are used instead of the elemental sulfur, to provide a tellurium to analine molar ratio of about 2.9:1. Essentially no difference in results is noted.

EXAMPLE 19

The procedure of Example 9 is repeated except that 1.2 grams ortho-toluidine are used instead of aniline. Essentially no difference in results is noted in the formation of methyl-N-ortho-tolyl carbamate.

EXAMPLE 20

The procedure of Example 9 is repeated except that 0.8 gram of N-butylamine are used instead of aniline. Essentially no difference in results is noted in the formation of methyl-N-butylcarbamate.

EXAMPLE 21

The procedure of Example 9 is repeated except that 1.1 grams of cyclohexylamine are used instead of aniline. Essentially no difference in results is noted in the formation of methyl-N-cyclo hexyl carbamate.

EXAMPLE 22

The procedure of Example 15 is repeated except that the alcohol reactant comprises, in separate runs, cyclohexanol, benzyl alcohol and butyl alcohol, respectively. Essentially no difference in results is noted in the formation of cyclohexyl-N-phenyl carbamate, benzyl-N-phenyl carbamate and butyl-N-phenyl carbamate, respectively.

EXAMPLE 23

The procedure of Example 9 is repeated except that 0.7 grams of toluene diamine are employed instead of aniline. After six hours of reaction at 180° C. the total conversion of $NH_2$ groups to the carbamate form is found to be 75%, at a selectivity to the monocarbamate

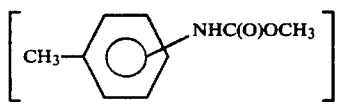

of about 40% and at a selectivity to the bis-carbamated form

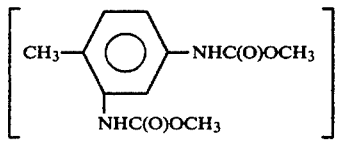

of about 50%.

EXAMPLE 24

The procedure of Example 23 is repeated except that 1.1 grams of 4,4'-methylene dianiline are used instead of toluene diamine. Essentially no difference in results is noted in the formation of the mono- and bis-methyl carbamate derived from the 4,4'-methylene dianiline, e.g.,

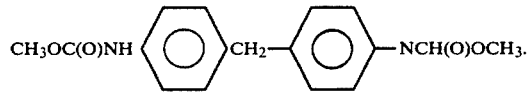

It will be obvious that various changes and modifications can be made without departing from the invention, and it is intended, therefore, that all matter contained in the foregoing description shall be interpreted as illustrative only and not as limitative of the invention.

I claim:

1. A process for producing carbamates from a reactant consisting essentially of an aromatic primary or secondary amine of the formula:
   (i) $RNH_2$,
   (ii) $RNH(R')$, or
   (iii) $R(NH_2)_m$ wherein R and R' are independently selected from the group consisting of aryl and alkaryl and wherein "m" is an integer of from 1 to 5, said aromatic amine being free of substitution by OH—, >C=O or sulfonic acid groups, said process comprising contacting said aromatic amine reactant in a reaction zone under substantially anhydrous conditions with (1) a source of carbon monoxide, (2) an organic compound which contains at least one hydroxyl group per molecule and which comprises a member selected from the group consisting of monohydric and polyhydric compounds of the formula $Z(OH)_n$, wherein "n" is an integer of at least one and "Z" is an aromatic, aliphatic, cycloaliphatic or aralilphatic group or a substituted derivative or any of the foregoing groups wherein the substituent comprises members selected from the group consisting of sulfoxide, amide, sulfone and carboxylic ester groups, and (3) a member selected from the group consisting of elemental sulfur, elemental selenium, elemental tellurium, sulfur compounds, selenium compounds and tellurium compounds, in the presence of a catalyst for the reaction, said catalyst consisting essentially of either an organic base or an inorganic base selected from the group consisting of nonhalide compounds and complexes of at least one metal selected from the group consisting of lithium, beryllium, sodium, magnesium, potassium, calcium, rubidium, iron, chromium, nickel, molybdenum, tungsten, aluminum, gallium, indium, thallium, copper, titanium, vanadium, cesium, manganese, strontium, barium, cobalt, rhenium and platinum, or mixtures thereof, and in the presence of at least one disulfide of the formula:

$$R^1\text{-S-S-}R^2$$

wherein $R^1$ and $R^2$ are independently selected from the group consisting of alkyl, aryl, alkaryl, aralkyl, cycloalkyl, alkenyl, alkynyl, heterocyclic, halogenated derivatives of the foregoing groups, and derivatives of the foregoing groups in which one or more carbon atom is replaced by an oxygen atom, to form the carbamate corresponding to said aromatic amine reactant and said hydroxyl-containing organic compound.

2. The process according to claim 1 wherein the amine comprises at least one member selected from the group consisting of aromatic primary amines of from 6 to 13 carbon atoms.

3. The process according to claim 1 wherein the amine comprises at least one member selected from the group consisting of aniline and alkyl-substituted anilines of up to 12 carbon atoms.

4. The process according to claim 1 wherein the hydroxyl group-containing compound comprises at least one member selected from the group consisting of monohydric and polyhydric alcohols having from 1 to 8 carbon atoms, halogenated derivatives of the foregoing alcohols, phenol and alkyl-substituted phenols having from 1 to 4 carbon atoms in each alkyl substituent.

5. The process according to claim 4 wherein the amine comprises at least one member selected from the group consisting of aniline and alkyl-substituted anilines of up to 12 carbon atoms and wherein said catalyst consists essentially of a mixture of (1) at least one inorganic basic compound of Fe, Co, Ni, Cr, Mo, W, Li, Be, Na, Mg, K, Ca, Rb, Sr, Cs and Ba and (2) a heterocyclic amine or a tertiary amine of the formula LNL'(L''), wherein L, L' and L'' are alkyl of 1 to 6 carbon atoms.

6. The process according to claim 1 wherein the catalyst comprises at least one member selected from the group consisting of tertiary amines, heterocyclic nitrogen-containing compounds, amidines and imines.

7. The process according to claim 1 wherein the organic disulfide comprises a bis-aryl disulfide having from 6 to 12 carbon atoms in the aryl moiety or a bis-alkyl disulfide having from 1 to 4 carbon atoms in the alkyl moiety.

8. The process according to claim 1 wherein the organic disulfide is employed in the reaction zone in an amount sufficient to provide a molar ratio of the organic disulfide to the amine reactant of at least about 0.1:1.

9. The process according to claim 1 wherein the catalyst consists essentially of an inorganic base compound of iron, cobalt or nickel, which also contains at least one metal form the group of chromium, molybdenum and tungsten, or at least one metal from the group of aluminum, gallium, indium and thallium.

10. The process according to claim 9 wherein the catalyst charged to the process is first contacted with a member of the group consisting of hydrogen, hydrogen selenide and hydrogen telluride at elevated temperature to incorporate the S, Se or Te into the catalyst.

11. The process according to claim 9 wherein the catalyst also contains an oxide or hydroxide of a metal selected from the group consisting of Li, Be, Na, Mg, K, Ca, Rb, Sr, Cs and Ba.

12. The process according to claim 11 wherein the catalyst is $BaO.CoMoO_4$, $SrO.NiWO_4$, $CsO.CoMoO_4$, $SrO.FeCrO_4$ or $NaOH.FeTl_2O_4$.

* * * * *

UNITED STATES PATENT AND TRADEMARK OFFICE
CERTIFICATE OF CORRECTION

PATENT NO. : 4,242,520

DATED : Dec. 30, 1980

INVENTOR(S) : David Moy

It is certified that error appears in the above-identified patent and that said Letters Patent are hereby corrected as shown below:

Col. 1, line 47 - "teritary" should be --tertiary--

Col. 2, line 3 - "nickle" should be --nickel--

Col. 2, line 64 - "cumen" should be --cumene--

Col. 3, line 23 - "teritary" should be --tertiary--

Col. 4, line 31 - "1974" should be --1979--

Col. 8, line 62 - "aresenates" should be --arsenates--

Col. 9, line 16 - "be-ng" should be --being--

Col. 11, line 55 - "hydrocargons" should be --hydrocarbons--

Col. 13, line 67 - "slectivity" should be --selectivity--

Col. 14, line 47 - "rectant" should be --reactant--

Col. 17, line 49 - "900 psig a" should be --900 psig and a--

Col. 17, line 60 - "carbomate" should be --carbamate

Col. 18, line 61 - "analine" should be --aniline--

UNITED STATES PATENT AND TRADEMARK OFFICE
CERTIFICATE OF CORRECTION

PATENT NO. : 4,242,520
DATED : Dec. 30, 1980
INVENTOR(S) : David Moy

It is certified that error appears in the above-identified patent and that said Letters Patent are hereby corrected as shown below:

Col. 22, line 4 - "form" should be --from--

Col. 22, lines 9-10 - "hydrogen, hydrogen selenide" should be --hydrogen sulfide, hydrogen selenide--

Signed and Sealed this

Second Day of March 1982

[SEAL]

Attest:

GERALD J. MOSSINGHOFF

Attesting Officer

Commissioner of Patents and Trademarks